March 28, 1972 R. S. MOORE Plant Pat. 3,084
MINIATURE ROSE PLANT
Filed Jan. 28, 1970
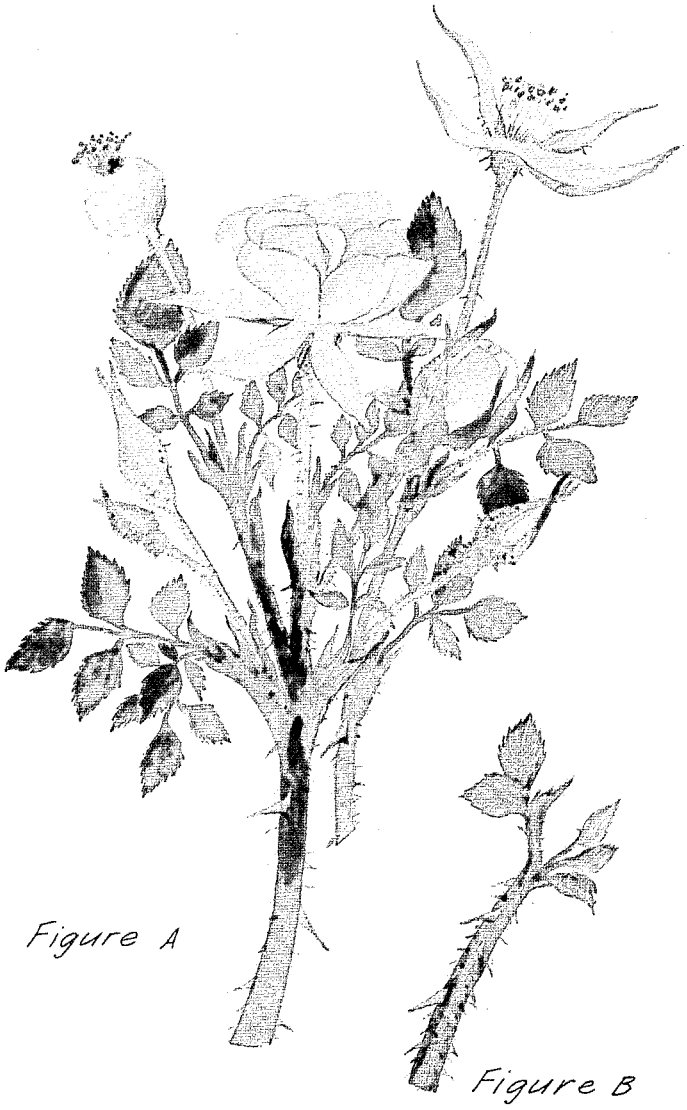
Figure A
Figure B
WITNESS
Jeanette Nunn Copley
INVENTOR
Ralph S. Moore United States Patent Office Plant Pat. 3,084
Patented Mar. 28, 1972

3,084
MINIATURE ROSE PLANT

Ralph S. Moore, 2519 E. Noble Ave.,
Visalia, Calif. 93277

Filed Jan. 28, 1970, Ser. No. 6,605
Int. Cl. A01h 5/00
U.S. Cl. Plt.—9 1 Claim

The present invention relates to a new and distinct variety of hardy, dwarf, bush type rose of the miniature class; the variety being primarily characterized—as to novelty—by rose pink to soft rose red buds and rose pink flowers which in general color effect are all over rose pink color (in varying shades) from the bud stage to the finished flower.

The variety is further characterized by:

The presence of numerous tiny prickles and oil glands on the bud (including calyx and peduncle) which gives the buds a "moss" effect (similar to that of older rose varieties of the Moss class—example: variety Salet (not patented)).

Little or no flower fragrance but soft pungent spicy fragrance from the "moss" (oil glands) on bud when rubbed or bruised.

An abundance of bloom, with flowers borne singly and in loose clusters.

A plant which is vigorous, of rounded spreading shape and with normal green, semi-glossy small foliage with pointed leaflets: the bud and flower being similar in size and form to the variety Pink Cameo (U.S. Plant Pat. No. 1,451). The plant which has a normal average height 10 to 14" at maturity can easily be maintained at a lower height with occasional trimming.

A plant which grows and blooms satisfactorily both in greenhouse and outdoors; is a good plant for growing in pots; and provides excellent garden decoration as well as cut flowers.

The present variety of miniature rose was originated by me at my nursery located at Visalia, Calif., under conditions of careful control and observation, as a cross between a seedling (Pinocchio×William Lobb), not patented, as the seed parent, and New Penny, not patented, as the pollen parent.

Subsequent to origination of the variety I successfully asexually reproduced it, in my nursery located as aforesaid, by budding as well as by cuttings; the reproductions having run true in all respects.

The figure of the drawing illustrates a spray, including foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bush; seedling; greenhouse; outdoors; cut flowers; garden decoration; potted plant.

Class: Miniature (Moss).

Flowers:

*Continuity.*—Intermittent to continuous throughout season.

*Fragrance.*—Little or none (flower fragrance) but the "moss" (oil glands on bud gives off fragrance when rubbed or crushed.

*Lasting quality.*—Average.

Flowers borne: Singly and in lose clusters, several together, on medium length slender stems.

Quantity of bloom: Average to above average both outside and in greenhouse.

Bud:

*Peduncle.*—Medium to long; slender; erect; light green; numerous short thorns interspersed with many short prickles each tipped with small knob (oil gland)—knob is darker color than portion below.

*Before calyx breaks.*—Size—small.

*Form.*—Pointed; with foliaceous appendages on surface of bud and foliaceous parts extending beyond tip of bud equal to one half or more of its length; in addition, calyx is covered with numerous short hairs each terminating in a small dark colored knob (oil gland).

*Color.*—Medium green. As calyx breaks: color light red (Rose Bengal 25/1), shading to near white at base; size—small.

*Form.*—Medium length; long pointed.

*Opening.*—Opens well in all weather.

Bloom:

*Size when fully open.*—Small, about 1½".

*Petalage.*—Double—15 to 18 petals (sometimes more; petals arranged regularly. Sometimes additional petaloids.

*Form.*—Flat or slightly cupped at first; later at maturity remaining relatively flat.

Petals: Satiny both inside and outside.

*Shape.*—Outside petals broad lanceolate, sometimes acute tip; intermediate—same as above.

Color: Newly opened flower from plant grown indoors (November 1969), Visalia, Calif.

*Outside petal.*—Outside surface—Phlox Pink 625/1 blending to near white at base; inside surface—Phlox Pink 625, shading lighter toward base—base yellow.

*Intermediate petal.*—Same as outside petal.

*Inside petal.*—Same as outside petal.

General color effect newly opened flower: Uniform medium pink.

Three days open: Becomes lighter pink shade.

Behaviour: Drop clean (may hang on if weather is damp).

Flower longevity:

*November—in greenhouse, 1969.*—4 to 5 days.

*Cut flowers at living room temperature.*—3 to 4 days.

Reproductive organs:

*Stamens.*—Numerous; arranged regularly about pistil.

*Filaments.*—Medium length.

*Anthers.*—Well formed, yellow.

*Pollen.*—Moderately abundant, yellow.

*Pistils.*—Average length and number.

*Styles.*—Medium length; bunched; yellowish.

*Stigma.*—Yellowish.

*Ovaries.*—All enclosed in calyx.

*Hips.*—Numerous.

*Sepals.*—Permanent; spear shaped.

*Seeds.*—Few; 1 to 3 per hip.

Foliage:

*Leaves.*—Compound of five leaflets (occasionally 3 or 7); abundant; small; semi-glossy.

*Leaflets*—Shape; lanceolate, apex acute; base rounded; margin serrate. Color: medium green. Rachis: medium strength; upper side grooved; under side moderately th orny.

*Stipules.*—Long; narrow; many short hairs along margins; long points, turning out at an angle of about 45 degrees.

Growth:

*Habit.*—Dwarf; bushy; spreading; much branched.

*Growth.*—Free; vigorous.

*Canes.*—Medium; slender.

*Main stems.*—Color: medium green. Thorns: quite thorny; slender; medium length; nearly straight or hooked slightly downward with shap points; interspersed with numerous smaller and shorter straight thorns or prickles; color—light to medium brown.

*Branches.*—Color: medium green. Thorns: quite thorny; medium length; straight or hooked slightly downward; sharp points; interspersed with numerous smaller and shorter straight thorns or prickles.

*New shoots.*—Color: medium green. Thorns: quite thorny; medium length; straight or hooked slightly downward; sharp points; base oval; color—reddish-brown. Prickles—usually present.

*Hairs.*—May be present (depending upon stage of growth).

The miniature rose plant and its flowers as herein described may vary in slight detail due to climatic, soil and cultural conditions under which the variety may be grown; the present description being of the variety as shown at Visalia, Calif.

The following is claimed:

1. A new and distinct variety of miniature rose plant of hardy, dwarf, rounded, much branched, bush type, as illustrated and described, characterized by resemblance to the Pink Cameo miniature rose (U.S. Plant Pat. No. 1,451) in general form of bud and flower but with color usually darker rose-pink in bud stage than Pink Cameo, the general color effect of the freshly opened flower being an all over pink or rose pink; further characterized by the flower buds having moss-like hairy appendages on bud surface which emits a fragrance whenever hairs (oil glands are rubbed or bruised; and further characterized by a plant which is vigorous and compact in growth, easy to propagate by building and from cuttings; with small medium green foilage, an abundance of bloom borne almost continuously throughout the growing season with flowers borne singly and in loose clusters.

No references cited.

ROBERT E. BAGWILL, Primary Examiner